US00PP35435P2

(12) United States Plant Patent
Wheeler et al.

(10) Patent No.: US PP35,435 P2
(45) Date of Patent: Oct. 24, 2023

(54) BLUEBERRY PLANT NAMED 'BB17-321PT-1'

(50) Latin Name: *Vaccinium corymbosum*
Varietal Denomination: BB17-321PT-1

(71) Applicant: BB IP Repository, LLC, Grand Junction, MI (US)

(72) Inventors: Edmund J. Wheeler, Holland, MI (US); Maria Pilar Banados, Santiago (CL); Melisa Andrea Osorio Perez, Santiago (CL)

(73) Assignee: BB IP Repository, LLC, Grand Junction, MI (US)

( * ) Notice: Subject to any disclaimer, the term of this patent is extended or adjusted under 35 U.S.C. 154(b) by 0 days.

(21) Appl. No.: 18/092,116

(22) Filed: Dec. 30, 2022

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP33,110 P2 * 6/2021 Wheeler ..... A01H 6/368 Plt./157

* cited by examiner

*Primary Examiner* — Kent L Bell
(74) *Attorney, Agent, or Firm* — King IP Law; Joshua King

(57) ABSTRACT

'BB17-321PT-1' is the third known blueberry genotype to be selected in a tropical environment of Peru. 'BB17-321PT-1' does not require chill-hours for either budbreak or fruit production. The fruit of 'BB17-321PT-1' is a medium to large size berry, with medium blue color and extremely crunchy and firm texture. Current season shoots lose apical dominance, easily promoting several laterals without the need of any summer pruning. The eating quality of 'BB17-321PT-1' is excellent and the crunchiness is superior to all varieties currently grown in Peru known to Applicant, with a sugar/acidity balance of 20 to 30. Time of fruit production in 'BB17-321PT-1' can be regulated by the pruning date and environment conditions.

6 Drawing Sheets

Latin name: *Vaccinium corymbosum.*
Common name: Blueberry.
Cultivar name: 'BB17-321PT-1'.

BACKGROUND AND SUMMARY

Blueberries are a well-known fruit enjoyed by many throughout the world. The novel blueberry variety in this application, 'BB17-321PT-1', is a new genotype selected in the tropical environment of Chao, Peru.

One example of an existing known blueberry variety in the same environment is 'Ventura', U.S. Plant Pat. No. 24,606. Compared to 'Ventura', 'BB17-321PT-1' is a much smaller plant and has lower vigor and is more precocious. The fruit of 'BB17-321PT-1' is presented on clusters of fruits on the plant and is produced in current season shoots rather than in 1-year-old shoots, which is another particular feature of 'BB17-321PT-1', similar to 'BB15-214PO-3'. The fruit of 'BB17-321PT-1' is sweet, with low acidity and a super crunchy texture, with medium to large berry size.

Comparing 'BB17-321PT-1' to 'Stellar' (brand name for 'BB06-50FL-1', U.S. Plant Pat. No. 30,445); the fruit of 'BB17-321PT-1' is smaller in size, has a darker blue color, has less persistent bloom (wax that cover the fruit) and more round shape; and the fruiting wood of 'BB17-321PT-1' is current season -shoots rather than in one-year-old shoots.

Additional examples of existing, patented blueberry varieties are 'Rocio', U.S. Plant Pat. No. 20,374, and 'Emerald', U.S. Plant Pat. No. 12,165. Compared with these varieties in Peru, the acidity of 'BB17-321PT-1' is lower than them as shown in Table 1, which provides fruit characteristics of 'BB17-321PT-1' compared to several other commercial varieties grown in Peru.

TABLE 1

Fruit characteristics of several blueberry varieties grown in Chao, Peru compared to 'BB17-321PT-1'. Data is average of several samples of fruit taken during harvest season 2021-2022.

| Cultivar | Fruit size (g) | Firmness Baxlo (shore) | Sugar Content (° brix) | Acidity (%) | Ratio ° Brix/ Acidity |
|---|---|---|---|---|---|
| 'Ventura' | 2.3 | 78 | 11.9 | 1.15 | 10.3 |
| 'Rocio' | 3.2 | 76 | 11.5 | 0.90 | 12.7 |
| 'Stellar' (brand name for 'BB06-50FL-1') | 5.3 | 75 | 12.0 | 0.72 | 16.6 |
| 'Emerald' | 2.1 | 75 | 10.1 | 1.20 | 8.4 |
| 'BB17-321PT-1' | 2.5 | 90 | 13.2 | 0.65 | 20.3 |

The present cultivar, 'BB17-321PT-1', provides one or more advantages compared to these and/or other blueberry varieties.

The fruit of 'BB17-321PT-1' is medium blue color, with very high firmness. The eating quality of 'BB17-321PT-1' is very good, having a sugar/acidity balance of 20 to 30, higher than other commercial cultivars in Peru like 'Ventura', 'Rocio', or 'Emerald'. 'BB17-321PT-1' is a compact plant with early maturity fruit and very excellent fresh market quality. Time of fruit production in 'BB17-321PT-1' can be regulated by the pruning date and moderated by the environment conditions in the tropical environment of Peru. This is another desirable characteristic of 'BB17-321PT-1', particularly in this new tropical environment for blueberries. 'BB17-321PT-1' does not require chill-hours for either budbreak or fruit production, which appears to be because 'BB17-321PT-1' does not develop endo-dormancy. 'BB17-321PT-1' was selected in soilless substrate production in pots in Chao, Peru and tested under soil and substrate soilless production in Peru and in Chile.

Areas of adaptation of 'BB17-321PT-1' include coast of Peru, Ecuador, and Colombia and other tropical areas with no winter chill conditions. 'BB17-321PT-1' was also tested in the temperate area of the Central Valley in Chile where it did not develop endodormancy.

Plants of 'BB17-321PT-1' are compact medium-upright with a medium size crown. 'BB17-321PT-1' produces several semi- upright canes, with greenish shoot colors and with good leafing and flowering.

The fruit of 'BB17-321PT-1' is sweet with low to medium acid, have a medium to large and very firm berry adapted to a tropical non-chill environment as well as temperate low-chill environment. The berry scar of 'BB17-321PT-1' is medium and dry. 'BB17-321PT-1' shows very long fruit storability of about 6 to 8 weeks. The productivity of 'BB17-321PT-1' is higher than 'Kestrel' (U.S. Plant Pat. No. 21,719) and similar to 'Rocio' in Peru, although it has not yet been tested commercially.

The flowering period of 'BB17-321PT-1' is extended and can last 4 to 6 months and is similar to 'Rocio' in the same tropical environment of Peru. Flowering of 'BB17-321PT-1' starts 75 to 80 days after pruning, which is shorter than 'Scintilla' (U.S. Plant Pat. No. 19,233) and 'Ventura', which take about 120 to 150 days. The fruiting period of 'BB17-321PT-1' is almost similar to 'Rocio', starting about 160 to 190 days after pruning and lasting for 5 to 7 months. Ripening of 'BB17-321PT-1' is extended and it is presented in two or three flushes during the of harvest in current season shoots.

BRIEF DESCRIPTION OF THE PHOTOGRAPHS

FIG. 3A showing one typical shoot of the new genotype and its loose apical dominance and FIG. 3B showing flowers on current season shoot and the size of the full flower.

Figure 1:
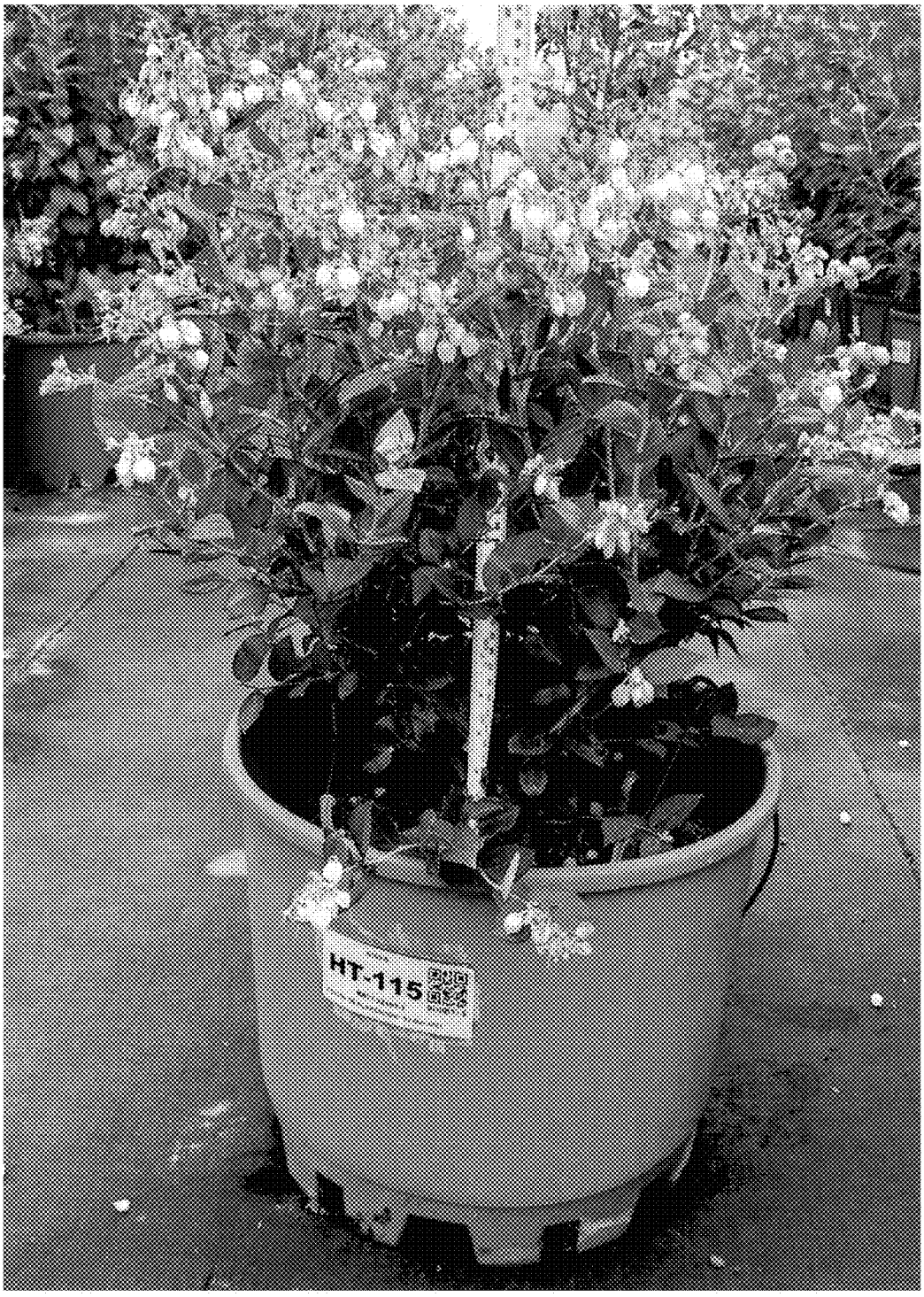
FIG. 1 is a close-up photograph of 'BB17-321PT-1' plants taken in October 2022 in Chao, Peru, and showing the plant growing in a pot with many flowers.
Figure 2:
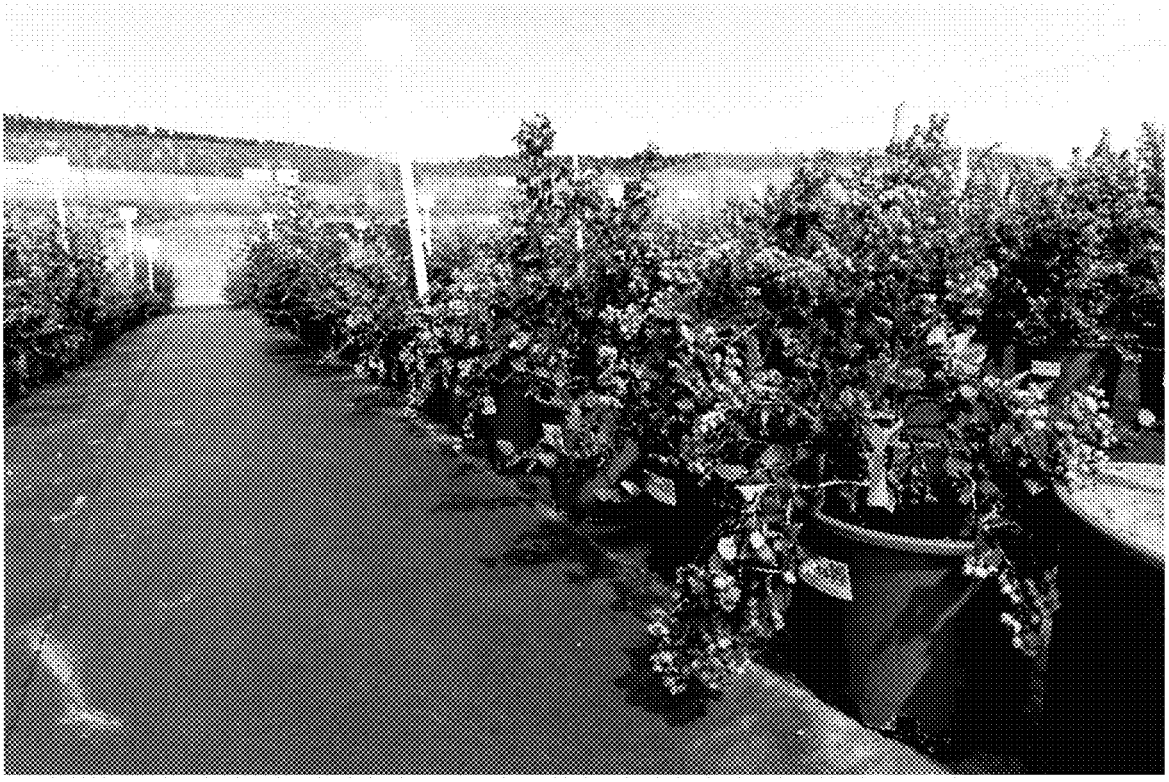
FIG. 2 is a photograph of 'BB17-321PT-1' plants taken in July 2022 in Chao, Peru, and showing the plant and its compact habit growing in a pot with many fruits.
Figure 3A:
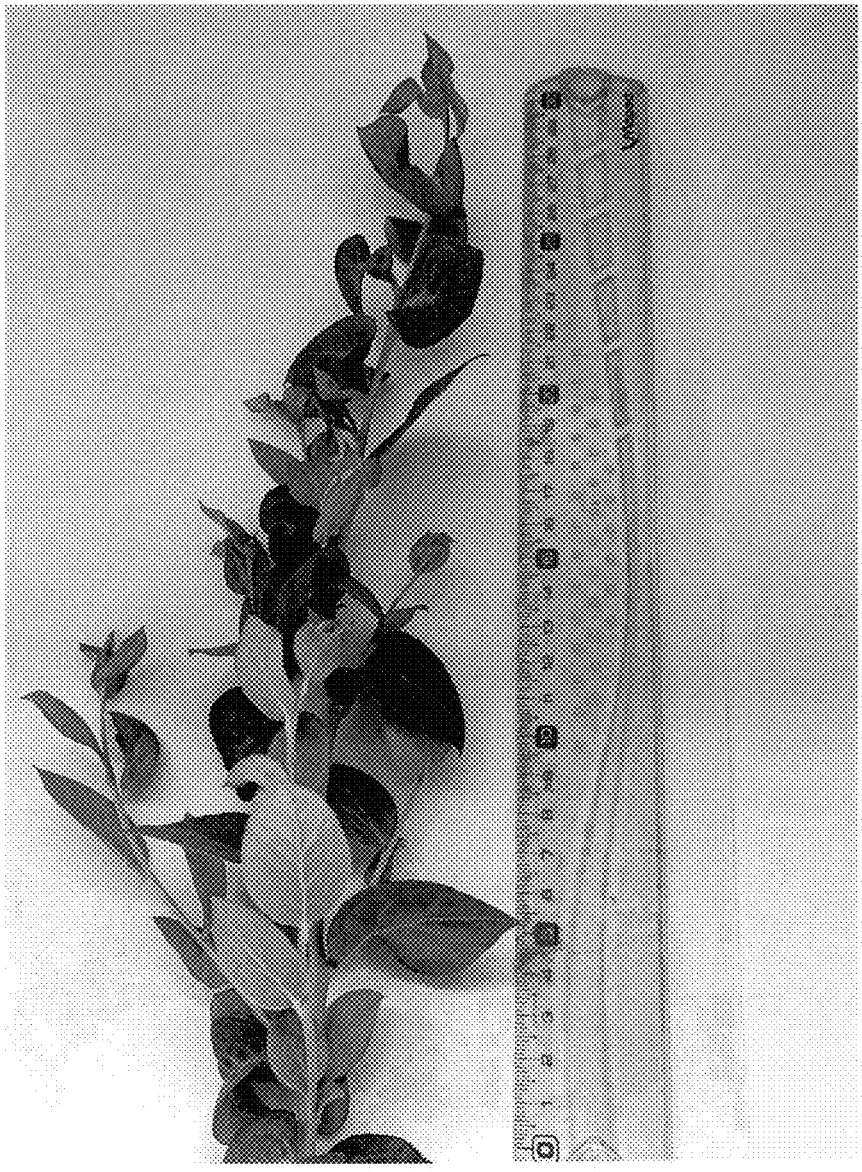
FIGS. 3A and 3B are close-up photographs of 'BB17-321PT-1' taken August 2022.
Figure 3B:
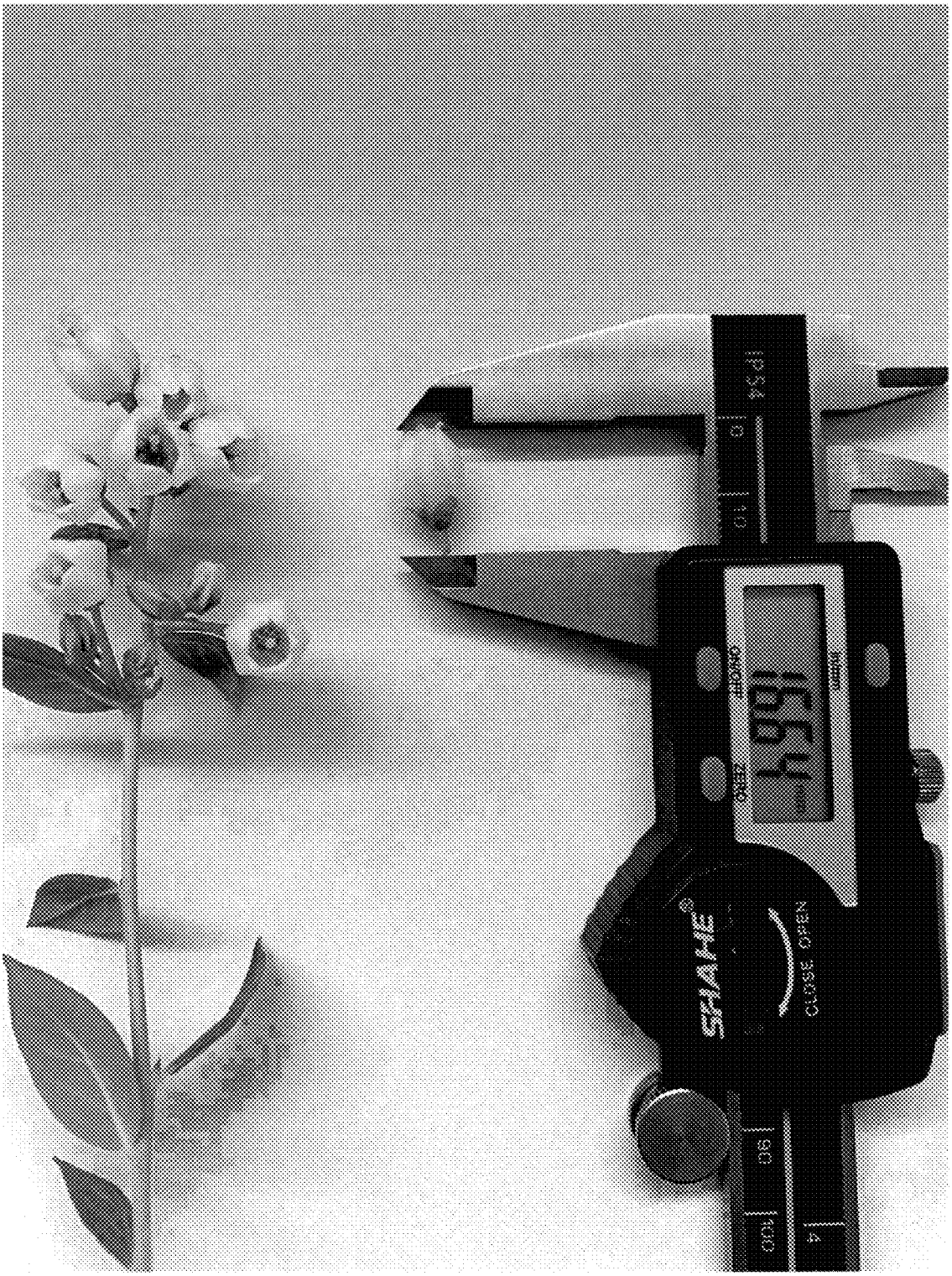
Figure 4A:
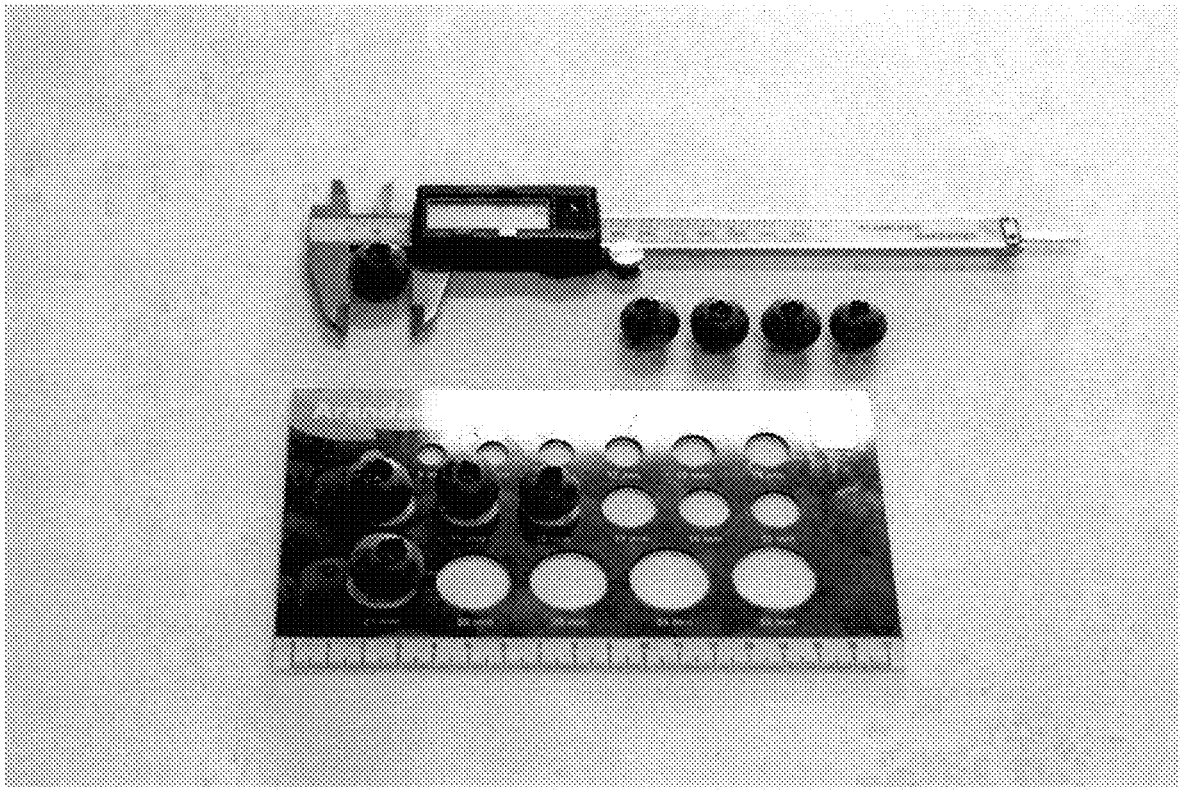
Figure 4B:
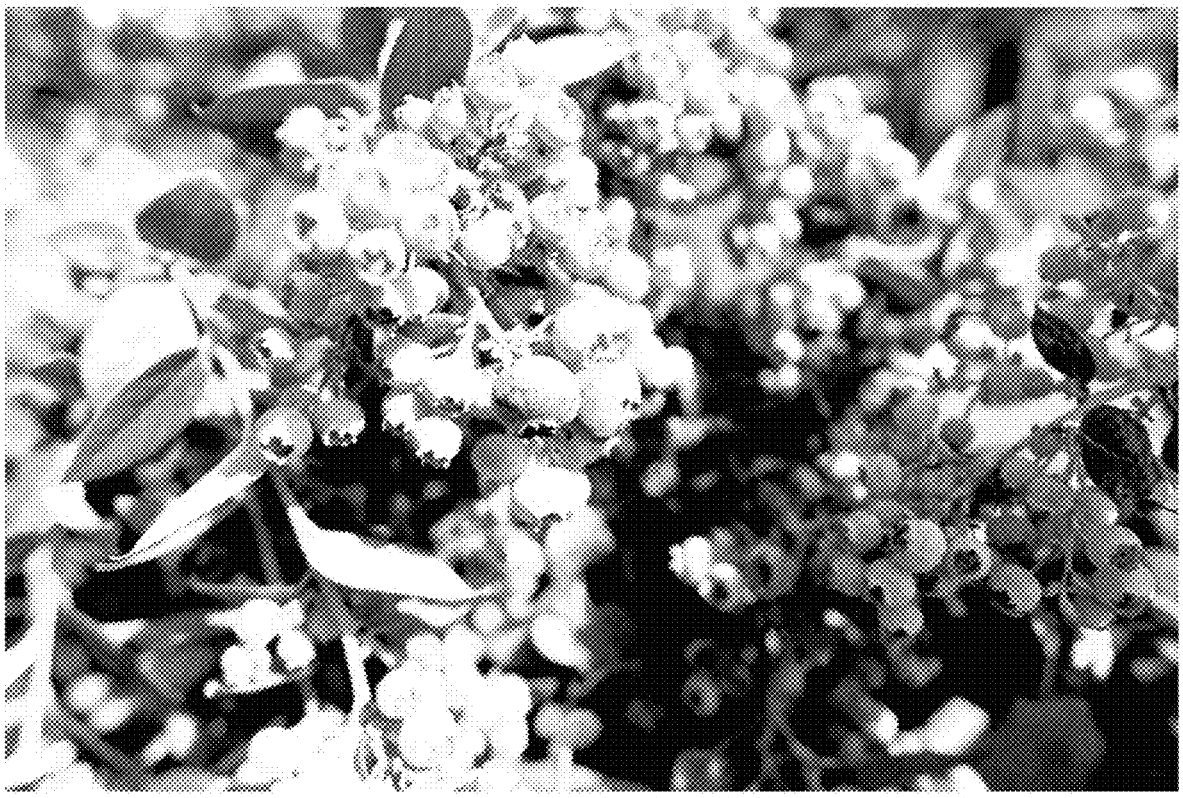

FIGS. 4A and 4B are photographs of 'BB17-321PT-1' fruit at different stages of maturity. FIG. 4A shows ripe fruit showing the size of the berries, and FIG. 4B shows fruit on the plant at different stages of maturity. Pictures taken near Chao, Peru in July 2021.

DETAILED DESCRIPTION

Note: statements of characteristics herein represent exemplary observations of the cultivar performance in Chao, Peru 8° 35'12"S 78° 35'58"W and will vary depending on time of year, location, annual temperature conditions and weather, etc.

Where dimensions, sizes, colors, and other characteristics are given, it is to be understood that such characteristics are approximations and averages. The descriptions reported herein are based on the original selected individual bush observed in successive years through 2019, 2020, 2021 and 2022 in fields near Chao, Peru and also in cloned plants planted in Chao, Peru in 2021 and 2022. Laboratory analysis of fruit characteristics were done in Chao, Peru.

Cultivar Name: 'BB17-321PT-1'

Classification:

Family: Ericaceae.

Botanical name: *Vaccinium corymbosum*

Common name: Blueberry.

Parentage:

Female Parent

Name: 'BB06-494MX-1' unpatented (child of 'Biloxi' (unpatented) x 'Primadonna' (U.S. Plant Pat. No. 20,181)).

Compared to 'BB06-494MX-1', 'BB17-321PT-1' has similar fruit size and is much firmer, sweeter, and less acidic.

Male Parent

Name: 'Keecrisp' unpatented (child of 'Sweetcrisp' (U.S. Plant Pat. No. 20,027) x 'Indigocrisp' (Fl 98-325, U.S. Plant Pat. No. 26,523).

Compared to 'Keecrips', fruit of 'BB17-3211PT-2' is firmer, sweeter and produce fruit on current season shoots 'BB17-321PT-1' originated as a seedling selected from a cross of 'BB06-494MX-1' and 'Keecrisp' made in a greenhouse in Grand Junction, Mich. in 2017.

Seed was germinated in Chile and plants of that cross were grown and then sent and planted in a seedling evaluation site in Chao, Province of La Libertad, Peru in November 2018 under soilless production system.

The plant was first selected in June 2019 based on its excellent fruit characteristics both in the field and after 5 days cold storage and was given the number 'BB17-321PT-1'. It was tested under this number for three years. The individual bush was observed and evaluated for productivity and fruit quality in the same site for three successive years from 2019 through 2021. An additional 40 bushes were propagated by in vitro and planted in an advanced trial in a soil and in soilless system near Chao, Peru in December 2020 and the fruit was evaluated in 2021 and 2022. All the observed bushes have retained the characteristics of the original selection.

'BB17-321PT-1' has been asexually propagated via tissue-cultured micro shoots since 2019. Propagated plants have been under evaluation in Chao, Peru since December 2020.

General Description of 'BB17-321PT-1'

'BB17-321PT-1' is a new and distinct non-chill tetraploid Southern/Tropical highbush blueberry variety (*Vaccinium*) of complex ancestry, based largely on *V. corymbosum* and *V. darrowii*, from the breeding program of BBIP Repository LLC. 'BB17-321PT-1' is a compact productive early-season variety of short cycle from pruning to harvest, with high quality fresh market characteristics 'BB17-321PT-1' is particularly well suited to be cultivated in tropical areas under soilless conditions in high density planting. 'BB17-321PT-1' has a compact semi-upright bush and a medium sized crown with many new vertical canes. The bush has a medium to low vigor and is very productive. It has shown very good adaptability to sandy soil and substrate mix of coco fiber. The fruit itself is medium blue color, with very high firmness and super crunchy texture. The eating quality is excellent with a higher sugar/acidity balance than 'Emerald', 'Ventura' or 'Rocio' in Peru. Fruit should be picked on a regular schedule about 7 to 9 days to maintain the quality of the fruit. 'BB17-321PT-1' is expected to be released as a third cultivar selected in Peru and it is an improvement over 'Emerald', 'Rocio' and 'Ventura' in terms of flavor and overall eating experience.

References to color refer to The Royal Horticultural Society Colour Chart 2007 Fifth Edition.

Morphological characteristics reference: Plant Systematics, Jones and Luchsinger, 2 Ed., McGraw Hill, New York, ISBN 0-07-032796-3, 1986.

Device used to measure Soluble Solids (SS-Brix°), Titratable acidity (TA), pH: PAL-BX/Acid 7, Atago USA, Inc., Bellevue, Wash.

Firmness readings: Shore by BAXLO Durometer (Chao, Peru)

General Description: Compact with a medium small size crown and moderate vigor; very sweet, low acid, super firm and super crunchy berry adapted to a tropical non-chill environment 'BB17-321PT-1' blooms about 75 to 80 days after pruning.

The average 50% ripening date is 250 days after pruning. Firmness ranges from 82 to 93 Baxlo Shore, Brix° from 12 to 15% and titratable acidity from 0.4 to 0.7% and sugar to acid ratio of 17 to 40. Storability is very long, and it could last up to 40 days or more in cold storage.

Specific features of the variety:

Plant:

*Growth habit.*—Compact, semi-upright.

*Plant width.*—65 cm at mid-bush height. Plant height: 65 cm.

*Productivity.*—1 to 2.0 kg per plant.

*Cold hardiness/tolerance.*—Not tested.

*Chilling requirement.*—'BB17-321PT-1' is a tropical highbush and this plant does not require chill hours for bud break.

*Canes.*—Moderately branched, average 3 to 4 main shoots per bush, average 50-60 cm length, medium number of laterals.

*Young current-season-shoots.*—Yellow-Green Group 145A.

*One-year-old shoot branches color.*—Yellow-Green Group 143C. Texture is soft. Mature cane color: Grey Brown N199-D.

*Mature cane texture.*—Rough.

*Fruiting wood.*—Current season shoots and one-year old shoots.

*Internode length range.*—2.5 to 4 cm.

*Surface texture of new wood.*—Smooth.

*Time of beginning of leaf bud burst.*—Bud break occurs 10 to 12 days after pruning in Chao, Peru.

*Time of beginning of flowering.*—50 to 60 days after planting or pruning in Chao, Peru.

*Date of 50% open flowers.*—75 to 80 days after planting or pruning in Chao, Peru for the first flush of flowers.

*Time of beginning of fruit ripening.*—Fruit ripening begins on 160 to 190 days after planting or pruning in Chao, Peru and on October 3 in Nancagua, Chile.

*Disease resistance/susceptibility.*—None claimed.

*Young current-season-shoots.*—Yellow green 145-A.

*One-year-old short branches color.*—Green Group 143-B.

Foliage:

*Young, newly expanded leaf color.*—Upper surface: Green group 138-A, lower surface: green group 138-B.

*Leaf arrangement.*—Simple Alternate.

*Mature, fully expanded leaves.*—Upper surface: green group N137-A, lower surface: green group 138-B.

*Leaf margins.*—Entire.

*Leaf venation.*—Pinnate.

*Leaf shape.*—Ovate.

*Mature leaf length.*—50 to 55 mm, average 53 mm.

*Mature leaf width.*—31 to 35 mm, average 32 mm.

*Leaf apices.*—Acuminate.

*Leaf bases.*—Acute.

*Vein and petiole coloration.*—

*Color vein.*—Yellow green 144-B.

*Color petiole.*—Yellow green 144-A.

*Petiole length.*—3 to 4 mm.

*Petiole diameter.*—2 mm.

*Evergreen.*—'BB17-321PT-1' is evergreen and keep its leaves during the entire year. Fall leaf color: Does not apply for this genotype since it keeps the leaves year round.

Leaf dimensions.

*Overall shape.*—Ovate.

*Length.*—50 to 55 mm, average 53 mm.

*Width.*—31 to 35 mm, average 32 mm.

*Leaf margins.*—Entire, no visible (microscope 10×) pubescence and a few nectaries.

*Leaf surface.*—Smooth upper and lower, no visible (microscope 10×) pubescence.

Leaf buds:

*Shape.*—Medium elongated.

*Length.*—2.5 to 4 mm.

*Width.*—1.7 to 1.9 mm.

*Color.*—Greyed-orange 169-B.

Flower buds:

*Shape.*—Round.

*Length.*—3 mm.

*Width.*—3.5 mm.

*Color.*—Greyed-orange 175-A.

Flower:

*Flower shape.*—Globose.

*Number per lateral.*—8 to 10.

*Flowers per cluster.*—8 to 10.

*Flower fragrance.*—Light floral.

*Corolla color.*—White 155-C.

*Corolla length.*—7 to 10.5 mm, average 8.1 mm.

*Corolla width.*—7.3 to 8 mm, average 7.8 mm.

*Corolla aperture width.*—4.6 mm.

*Corolla texture.*—Smooth.

*Flower peduncle length.*—7 to 10 mm, average 8.2 mm.

*Peduncle diameter.*—1 mm.

*Peduncle texture.*—Smooth.

*Peduncle color.*—Green group 139-D.

*Flower pedicel length.*—5 mm.

*Pedicel diameter.*—1.1 mm.

*Pedicel texture.*—Smooth.

*Pedicel color.*—Green group 143-B.

*Calyx (with sepals).*—4.83 mm.

*Calyx color.*—Green group 143-B.

*Stamen length.*—5 to 6 mm.

*Stamen number per flower.*—11 to 13.

*Stamen filament color*.—Greyed 193-C.
*Style*.—11.3 mm, top of ovary to stigma tip.
*Style color*.—Green group 139-D.
*Pistil extends over the top of corolla*.—0.5 mm.
*Ovary color*.—Yellow Green 147-B.
*Anther length*.—3.28 mm.
*Number*.—1.
*Anther color*.—Greyed-orange 170-C.

Pollen:
*Abundance*.—Medium.
*Color*.—Yellow 8-D.

Fruit:
*Date of* 50% *maturity*.—230 to 270 days after pruning.
*Duration of ripening*.—Average 65 to 80 days from bloom to ripen in Chao, Peru. Ripening period can last 6 months.
*Yield*.—1 to 2.4 kg per plant.
*Cluster density*.—Dense.
*Immature fruit color*.—Greyed Green grey 194-B.
*Berry color with wax*.—Blue group 103-C.
*Berry color with wax removed*.—Blue 103-A.
*Berry flesh color*.—Green 139-C.
*Berry surface wax abundance*.—Moderately persistent.
*Berry weight*.—Average 2 to 3 grams/berry.
*Berry size diameter*.—16 to 20 mm.
*Berry height*.—12.7 mm.
*Berry width*.—17.8 mm.
*Aspect* (*h/w*).—0.71.
*Berry shape*.—Oblate.
*Average number of fruits per cluster*.—8 to 10.
*Detachment force*.—Easy.
*Self-fruitfulness*.—Fair, cross pollination may be desirable for maximum yield and fruit size.
*Fruit stem scar*.—3.1 mm diameter, 1 mm depth.
*Calyx*.—5 lobed.
*Calyx diameter*.—7.2 mm.
*Calyx depth*.—0.5 mm.
*Berry firmness*.—Firm, 89 to 95 Shore of Baxlo.
*Berry sweetness*.—High, Brix°=12 to 15.
*Berry acidity*.—Titratable acidity=0.4% to 0.7%
*Berry flavor and texture*.—Good blueberry flavor, sweet and low acidity, and very crunchy texture.
*Storage ability*.—High, 6 to 8 weeks in refrigerated storage.
*Suitability for mechanical harvesting*.—Not tested.

Seed:
*Seed abundance in fruit*.—High, 47 to 50 seeds per fruit.
*Seed color*.—Greyed-Orange group N170-A.
*Seed dry weight*.—6 mg.
*Seed size*.—1.4 mm length, 0.6 mm width.

Possible typical market uses: Mainly fresh market. It can also be used for processing and/or as frozen fruit.

What is claimed is:

1. A new and distinct cultivar of tropical southern highbush blueberry plant named 'BB17-321PT-1' as described and shown herein.

* * * * *